(12) United States Patent
Fu et al.

(10) Patent No.: US 10,932,881 B2
(45) Date of Patent: Mar. 2, 2021

(54) GUIDE FOR SURGICAL PURPOSE

(71) Applicant: KAOHSIUNG MEDICAL UNIVERSITY, Kaohsiung (TW)

(72) Inventors: Yin-Chih Fu, Kaohsiung (TW);
Tien-Ching Lee, Kaohsiung (TW);
Yan-Hsiung Wang, Kaohsiung (TW);
Chih-Kung Wang, Kaohsiung (TW);
Ya-Chuan Hsu, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 173 days.

(21) Appl. No.: 16/346,107

(22) PCT Filed: Sep. 18, 2017

(86) PCT No.: PCT/CN2017/102006
§ 371 (c)(1),
(2) Date: Apr. 29, 2019

(87) PCT Pub. No.: WO2018/076957
PCT Pub. Date: May 3, 2018

(65) Prior Publication Data
US 2019/0254770 A1  Aug. 22, 2019

Related U.S. Application Data

(60) Provisional application No. 62/415,477, filed on Oct. 31, 2016.

(51) Int. Cl.
*A61B 90/11* (2016.01)
*A61B 1/04* (2006.01)
(Continued)

(52) U.S. Cl.
CPC .............. *A61B 90/11* (2016.02); *A61B 1/04* (2013.01); *A61B 1/317* (2013.01); *A61B 17/02* (2013.01);
(Continued)

(58) Field of Classification Search
CPC ........... A61B 17/02; A61B 1/04; A61B 1/317; A61B 17/320016; A61B 17/320036;
(Continued)

(56) References Cited

U.S. PATENT DOCUMENTS 5,730,749 A * 3/1998 Battenfield .... A61B 17/320036
606/167
2010/0100046 A1 * 4/2010 Berger ........... A61B 17/320036
604/164.12
2014/0296901 A1 * 10/2014 Derwin ............. A61B 17/3421
606/185

* cited by examiner

*Primary Examiner* — George J Ulsh
(74) *Attorney, Agent, or Firm* — Hannah Tien

(57) ABSTRACT

This invention provides a guide for surgical purpose, comprising: a long column body, being in a hollow shape, an upper side thereof having a semi-cylinder, a bottom side thereof having a cuboid, and an inside thereof being provided with an elongated slot, in which an interior of the semi-cylinder is in communication with an interior of the cuboid; a wing-shaped part, being in a wing shape, and disposed at one end of the long column body and engaged with one side of the cuboid and extending from both ends of the one side of the cuboid, for grasping during surgery; a limiting piece, being in a ring shape and socketing the other end of the long column body and engaging with the other side of the cuboid, for withstanding the tissues during surgery; and a replaceable expander, being disposed in the elongated slot, for expanding and opening a surgical incision of tissues, wherein the replaceable expander is replaceable with another expander of different dimension in a stepwise
(Continued)

manner via the one side of the cuboid proximate to the wing-shaped part and inside the elongated slot, thereby for expanding.

20 Claims, 2 Drawing Sheets

(51) Int. Cl.
    *A61B 1/317*     (2006.01)
    *A61B 17/32*     (2006.01)
    *A61M 29/00*     (2006.01)
    *A61B 17/02*     (2006.01)

(52) U.S. Cl.
    CPC ..... *A61B 17/320016* (2013.01); *A61M 29/00* (2013.01); *A61B 2017/320052* (2013.01)

(58) Field of Classification Search
    CPC ................ A61B 17/3417; A61B 90/11; A61B 2017/0023; A61B 2017/320044; A61B 2017/320052; A61M 29/00
    See application file for complete search history.

GUIDE FOR SURGICAL PURPOSE

CROSS-REFERENCES TO RELATED APPLICATIONS

This patent application is a U.S. National Stage Application of PCT/CN2017/102006 filed Sep. 18, 2017 and claims the benefit of priority from U.S. Provisional Application Ser. No. 62/415,477 filed Oct. 31, 2016, the contents of each of which is incorporated herein by reference in their entirety.

FIELD OF THE INVENTION

The present invention relates to treatments for nerve compression and injuries in animals, including methods of treatment and surgical instruments, and more particularly to methods and devices for treating human carpal tunnel syndrome.

BACKGROUND TECHNOLOGY

Carpal tunnel syndrome is the most common peripheral nerve compression lesion in the human wrist. The main cause of carpal tunnel syndrome is the compression of the wrist transverse ligament as the hand nerve (median nerve) enters the palm of the hand at the wrist. The clinical symptoms of the carpal tunnel syndrome are swelling, pain, scorching and pain numbness in the involved hand, and which are limited to an area innervated by the median nerve, including the index finger, the middle finger, and the thumb. Clinically, a surgical method is generally applied to a patient whose symptoms are long-term and severe. The surgery is to incise the transverse wrist ligament which compress the median nerve to relieve the pressure of the carpal tunnel, thereby improving the symptoms. The first line of treatment is nonoperative, including rest, life style modification to avoid aggravating activity, splinting wrists in neutral positions, anti-inflammatory medication use, and steroid injections.

The operative method is to release the pressure on the median nerve by incising the transverse ligament of the wrist through open or endoscopic surgery. More specifically, the open procedure is to make an incision over the skin of the wrist and then incise the transverse ligament as described above. Surgical release also can be done to make a small incision and then insert endoscope. The median nerve is identified and dissected from the wrist ligament. The ligament is then incised and the pressure is released from the median nerve.

The commercially available tool for the operation of the wrist tunnel syndrome is equipped with a monitoring device such as a light source, a camera lens and a display, so that the surgeon can see the actual cutting position of the blade during the operation. Yet, these devices must be disinfected and sterilized before operation and also accompany with the difficulty and learning curve of this procedure. If there is a disposable surgical instrument to make the procedure easier, and reduce the patient's discomfort during operation, and increase the convenience of the surgeon.

SUMMARY OF THE INVENTION

The invention provides a guide for surgical purpose, comprising: a long column body, being in a hollow shape, an upper side thereof having a semi-cylinder, a bottom side thereof having a cuboid, and an inside thereof being provided with an elongated slot, in which an interior of the semi-cylinder is in communication with an interior of the cuboid; a wing-shaped part, being in a wing shape, and disposed at one end of the long column body and engaged with one side of the cuboid and extending from both ends of the one side of the cuboid, for grasping during surgery; and a replaceable expander, being disposed in the elongated slot, for expanding and opening a surgical incision of tissues, wherein the replaceable expander is replaceable with another expander of different dimension in a stepwise manner via the one side of the cuboid proximate to the wing-shaped part and inside the elongated slot, thereby for expanding.

In one embodiment, the replaceable expander is in a round rod shape and is formed in sequence by connection of a tail rod handle, a threaded rod, and a rod body for expanding.

In one embodiment, the long column body and the wing-shaped part are integrated in one piece.

In one embodiment, it further comprises a limiting piece, being in a ring shape and socketing the other end of the long column body and engaging with the other side of the cuboid, for withstanding the tissues during surgery. Preferably, the long column body, the wing-shaped part and the limiting piece are integrated into one piece.

In one embodiment, the semi-cylinder on the upper side of the long-column body is provided with thread on an external surface proximate to the wing-shaped part, so as to allow the long column body to extend into the tissues in a friction manner.

In one embodiment, it further comprises a knife, which is disposed in the elongated slot for cutting open a portion to be cut.

In one embodiment, it further comprises a photo-taking element, which is provided at a proper place of the elongated slot, and an externally connected picture displaying element, so as to facilitate proceeding of the surgery.

In one embodiment, the guide for surgical purpose is used in operation of a hand, wrist, elbow, shoulder, vertebral, hip, lap, crotch or foot.

In one embodiment, the guide for surgical purpose is used in treating human carpal tunnel syndrome.

The invention provides a guide for surgical purpose, comprising: a long column body, being in a hollow shape, an upper side thereof having a semi-cylinder, a bottom side thereof having a cuboid, and an inside thereof being provided with an elongated slot, in which an interior of the semi-cylinder is in communication with an interior of the cuboid; a limiting piece, being in a ring shape and socketing the other end of the long column body and engaging with the other side of the cuboid, for withstanding the tissues during surgery; and a replaceable expander, being disposed in the elongated slot, for expanding and opening a surgical incision of tissues, wherein the replaceable expander is replaceable with another expander of different dimension in a stepwise manner via the one side of the cuboid proximate to the wing-shaped part and inside the elongated slot, thereby for expanding.

In one embodiment, the replaceable expander is in a round rod shape and is formed in sequence by connection of a tail rod handle, a threaded rod, and a rod body for expanding.

In an embodiment, the long column body and the limiting piece are integrated in one piece.

In one embodiment, it further comprises a wing-shaped part, being in a wing shape, and disposed at one end of the long column body and engaged with one side of the cuboid and extending from both ends of the one side of the cuboid, for grasping during surgery. Preferably, the long column body, the wing-shaped part and the limiting piece are integrated into one piece.

In an embodiment, the semi-cylinder on the upper side of the long-column body is provided with thread on an external surface proximate to the wing-shaped part, so as to allow the long column body to extend into the tissues in a friction manner.

In one embodiment, it further comprises a knife, which is disposed in the elongated slot for cutting open a portion to be cut.

In one embodiment, it further comprises a photo-taking element, which is provided at a proper place of the elongated slot, and an externally connected picture displaying element, so as to facilitate proceeding of the surgery.

In one embodiment, the guide for surgical purpose is used in operation of a hand, wrist, elbow, shoulder, vertebral, hip, lap, crotch or foot.

In one embodiment, the guide for surgical purpose is used in treating human carpal tunnel syndrome.

SYMBOL DESCRIPTION

Figure 1:
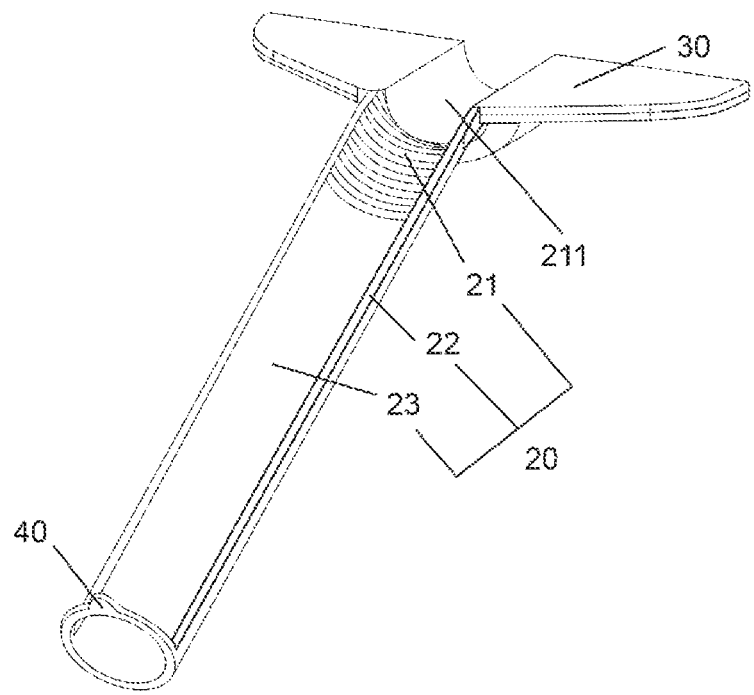
FIG. 1 is a schematic view of a guide for surgical purpose of the present invention.

10 Guide for surgical purpose
20 Long column body
21 Semi-cylinder
211 Thread
22 Cuboid
23 Elongated slot
30 Wing-shaped part
40 Limiting piece
50 Expander
51 Tail rod handle
52 Rod body
53 Threaded rod

PREFERRED EMBODIMENTS

The following embodiments are not for limiting the use, but for presenting variety of the invention.

Example 1

Figure 2:
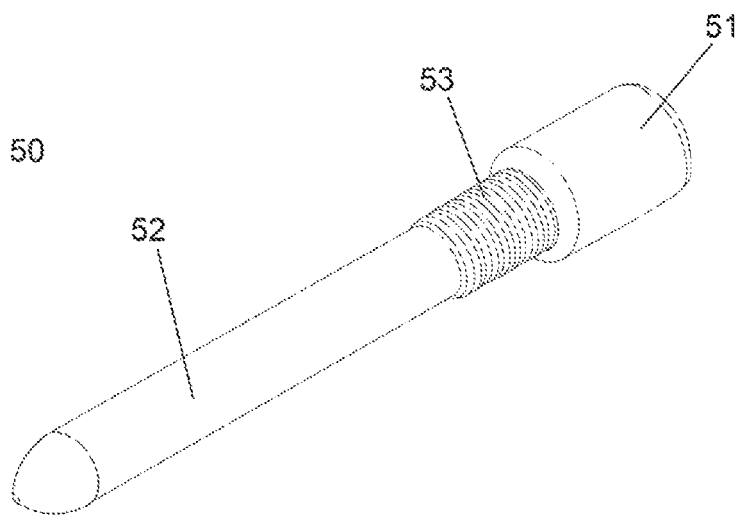
FIG. 2 is a schematic illustration of a replaceable expander in a guide for surgical purpose of the present invention.
Figure 3:
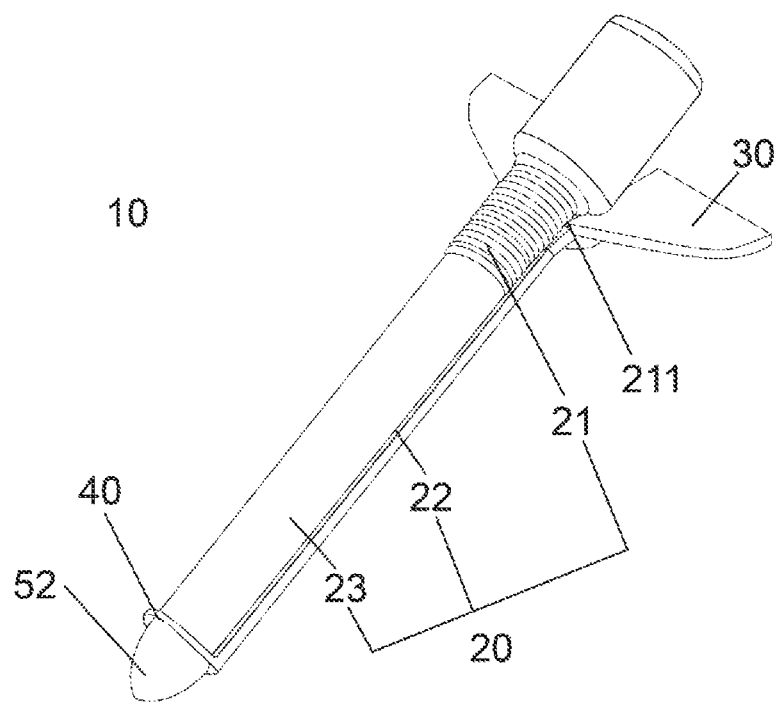
FIG. 3 is a schematic view showing the combination of the guide for surgical purpose of the present invention.

Please refer to FIGS. 1-3. As shown in FIG. 1, the invention provides a guide for surgical purpose (10), comprising: a long column body (20), being in a hollow shape, an upper side thereof having a semi-cylinder (21), in which at one end thereof and proximate to a hand-held part is provided with thread (211), a bottom side thereof having a cuboid (22), and an inside thereof being provided with an elongated slot (23), in which an interior of the semi-cylinder is in communication with an interior of the cuboid; a wing-shaped part (30), being in a wing shape and disposed at one end of the long column body and engaged with one side of the cuboid and extending from both ends of the one side of the cuboid, for grasping during surgery; a limiting piece (40), being in a ring shape and socketing the other end of the long column body and engaging with the other side of the cuboid, for withstanding the tissues during surgery; and a replaceable expander (50), as shown in FIG. 2, which is in a round rod shape and formed in sequence by connection of a tail rod handle (51), a threaded rod (53), and a rod body (52) for expanding, and is disposed in the elongated slot, for expanding and opening a surgical incision of tissues.

FIG. 3 is a schematic diagram in combination of a guide for surgical purpose according to the invention, in which the replaceable expander (50) is disposed in the elongated slot (23) of the cuboid (22) of the long column body (20). In the practical operation, the thread rod (53) of the replaceable expander (50) is mutually engaged with the semi-cylinder (21) on the upper side of the long column body (20) at a place of the thread (211) provided in an external surface proximate to the wing-shaped part (30), i.e. proximate to the hand-help part, thereby forming the guide for surgical purpose (10). The thread (211) may be rotated to extend the rod body (52) into the tissues of the hand for expanding. After expansion, a knife (not shown in the drawing) may be utilized to replace the expander (50) and is forwarded ahead along the elongated slot for cutting the portion of the wrist transverse ligament to be cut open, and via the limiting piece (40), a doctor is informed that the cut position has been arrived so as to avoid cutting further the tissues not intended to be cut. During cutting, a picture-taking element (not shown in the drawing) may be provided at a proper place of the elongated slot for taking pictures, while an externally connected picture-displaying element may be provided for facilitating the proceeding of the surgery. The expander may be replaced with different dimensions in a stepwise manner, such as in an order from 5 mm, 6 mm to 7 mm, via one side of the cuboid proximate to the wing-shaped part and inside the elongated slot.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The instruments, materials and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A guide for surgical purpose, comprising:
   a long column body, being in a hollow shape, an upper side thereof having a semi-cylinder, a bottom side thereof having a cuboid, and an inside thereof being provided with an elongated slot, in which an interior of the semi-cylinder is in communication with an interior of the cuboid;
   a wing-shaped part, being in a wing shape, and disposed at one end of the long column body and engaged with one side of the cuboid and extending from both ends of the one side of the cuboid, for grasping during surgery; and
   a replaceable expander, being disposed in the elongated slot, for expanding and opening a surgical incision of tissues, wherein the replaceable expander is replaceable with another expander of different dimension in a stepwise manner via the one side of the cuboid proximate to the wing-shaped part and inside the elongated slot, thereby for expanding.

2. A guide for surgical purpose as claimed in claim 1, wherein the replaceable expander is in a round rod shape and is formed in sequence by connection of a tail rod handle, a threaded rod, and a rod body for expanding.

3. A guide for surgical purpose as claimed in claim 1, wherein the long column body and the wing-shaped part are integrated in one piece.

4. A guide for surgical purpose as claimed in claim 1, further comprising a limiting piece, being in a ring shape and socketing an other end of the long column body and engaging with an other side of the cuboid, for withstanding the tissues during surgery.

5. A guide for surgical purpose as claimed in claim 4, wherein the long column body, the wing-shaped part and the limiting piece are integrated into one piece.

6. A guide for surgical purpose as claimed in claim 1, wherein the semi-cylinder on the upper side of the long-column body is provided with thread on an external surface proximate to the wing-shaped part, so as to allow the long column body to extend into the tissues in a friction manner.

7. A guide for surgical purpose as claimed in claim 1, further comprising a knife, which is disposed in the elongated slot for cutting open a portion of a transverse ligament of a wrist to be cut.

8. A guide for surgical purpose as claimed in claim 1, further comprising a photo-taking element, which is provided at a place near a front part of the elongated slot, and an externally connected picture displaying element, so as to facilitate proceeding of the surgery.

9. A guide for surgical purpose as claimed in claim 1, wherein the guide for surgical purpose is used in operation of a hand, wrist, elbow, shoulder, vertebral, hip, lap, crotch or foot.

10. A guide for surgical purpose as claimed in claim 1, wherein the guide for surgical purpose is used in treating human carpal tunnel syndrome.

11. A guide for surgical purpose, comprising:
   a long column body, being in a hollow shape, an upper side thereof having a semi-cylinder, a bottom side thereof having a cuboid, and an inside thereof being provided with an elongated slot, in which an interior of the semi-cylinder is in communication with an interior of the cuboid;
   a limiting piece, being in a ring shape and socketing the other end of the long column body and engaging with the other side of the cuboid, for withstanding the tissues during surgery; and
   a replaceable expander, being disposed in the elongated slot, for expanding and opening a surgical incision of tissues,
   wherein the replaceable expander is replaceable with another expander of different dimension in a stepwise manner via the one side of the cuboid proximate to the wing-shaped part and inside the elongated slot, thereby for expanding.

12. A guide for surgical purpose as claimed in claim 11, wherein the replaceable expander is in a round rod shape and is formed in sequence by connection of a tail rod handle, a threaded rod, and a rod body for expanding.

13. A guide for surgical purpose as claimed in claim 11, wherein the long column body and the limiting piece are integrated in one piece.

14. A guide for surgical purpose as claimed in claim 11, further comprising a wing-shaped part, being in a wing shape, and disposed at one end of the long column body and engaged with one side of the cuboid and extending from both ends of the one side of the cuboid, for grasping during surgery.

15. A guide for surgical purpose as claimed in claim 14, wherein the long column body, the wing-shaped part and the limiting piece are integrated into one piece.

16. A guide for surgical purpose as claimed in claim 11, wherein the semi-cylinder on the upper side of the long-column body is provided with thread on an external surface proximate to the wing-shaped part, so as to allow the long column body to extend into the tissues in a friction manner.

17. A guide for surgical purpose as claimed in claim 11, further comprising a knife, which is disposed in the elongated slot for cutting open a portion of a transverse ligament of a wrist to be cut.

18. A guide for surgical purpose as claimed in claim 11, further comprising a photo-taking element, which is provided at a place near a front part of the elongated slot, and an externally connected picture displaying element, so as to facilitate proceeding of the surgery.

19. A guide for surgical purpose as claimed in claim 11, wherein the guide for surgical purpose is used in operation of a hand, wrist, elbow, shoulder, vertebral, hip, lap, crotch or foot.

20. A guide for surgical purpose as claimed in claim 11, wherein the guide for surgical purpose is used in treating human carpal tunnel syndrome.

* * * * *